(12) United States Patent
Garfinkle

(10) Patent No.: US 6,982,643 B2
(45) Date of Patent: *Jan. 3, 2006

(54) CARGO SECURITY METHOD AND APPARATUS

(75) Inventor: Jeffrey Garfinkle, New York, NY (US)

(73) Assignee: Freight Glove Technologies, LLC, New York, NY (US)

( * ) Notice: Subject to any disclaimer, the term of this patent is extended or adjusted under 35 U.S.C. 154(b) by 241 days.

This patent is subject to a terminal disclaimer.

(21) Appl. No.: 10/266,347

(22) Filed: Oct. 8, 2002

(65) Prior Publication Data

US 2004/0066887 A1    Apr. 8, 2004

(51) Int. Cl.
*G08B 13/14*    (2006.01)

(52) U.S. Cl. .................. 340/568.1; 340/3.1; 53/399; 53/397; 150/154

(58) Field of Classification Search ............ 340/568.1, 340/3.1, 540, 571; 378/57; 53/399, 397; 150/154

See application file for complete search history.

(56) References Cited

U.S. PATENT DOCUMENTS

| | | | | |
|---|---|---|---|---|
| 4,526,416 A | * | 7/1985 | Rode ..................... 296/100.16 |
| 4,750,197 A | * | 6/1988 | Denekamp et al. ...... 455/404.2 |
| 5,186,290 A | * | 2/1993 | Takayama .................. 190/108 |
| 5,474,185 A | * | 12/1995 | Franke ........................ 206/586 |
| 5,524,133 A | * | 6/1996 | Neale et al. ................... 378/53 |
| 5,656,996 A | * | 8/1997 | Houser ....................... 340/541 |
| 5,660,136 A | * | 8/1997 | Pignatelli et al. ........... 114/361 |
| 5,677,674 A | * | 10/1997 | Wolf ........................... 340/541 |
| 5,692,029 A | * | 11/1997 | Husseiny et al. ............. 378/88 |
| 5,838,759 A | * | 11/1998 | Armistead .................... 378/57 |
| 6,058,158 A | * | 5/2000 | Eiler ............................ 378/57 |
| 6,144,298 A | * | 11/2000 | Haimovich et al. ......... 340/564 |
| 6,292,533 B1 | * | 9/2001 | Swift et al. ................... 378/57 |
| 6,394,528 B2 | * | 5/2002 | Hoenack ................. 296/136.01 |
| 6,556,138 B1 | * | 4/2003 | Sliva et al. .............. 340/568.1 |
| 6,567,496 B1 | * | 5/2003 | Sychev ......................... 378/57 |
| 2001/0014137 A1 | * | 8/2001 | Bjorkholm ................... 378/57 |
| 2002/0120475 A1 | * | 8/2002 | Morimoto ...................... 705/4 |
| 2003/0164763 A1 | * | 9/2003 | Hisano et al. .......... 340/539.13 |

* cited by examiner

*Primary Examiner*—Daniel Wu
*Assistant Examiner*—Sihong Huang
(74) *Attorney, Agent, or Firm*—McAndrews, Held & Malloy, Ltd

(57) ABSTRACT

A comprehensive and effective system at detecting unauthorized hazardous materials such as explosives potentially placed by terrorists in cargo or freight, such as air cargo, is disclosed. The system is cost effective and is non-disruptive to shippers of cargo. The system provided in one or more embodiments is capable of virtually guaranteeing the continuous security and integrity of cargo or freight during the storage and transit process. The system provides a combination of advanced x-ray technology and packaging technology. A method is disclosed comprising the steps of applying X-rays with an X-ray machine to freight and placing a cover on the freight. The step of placing the cover on the freight may include locking the cover on the freight with a lock. The lock may include an electronic memory, which is programmed with a unique code, which identifies the freight and indicates whether it has been tampered with.

10 Claims, 8 Drawing Sheets

CARGO SECURITY METHOD AND APPARATUS

FIELD OF THE INVENTION

This invention relates to improved methods and apparatus concerning preventing cargo from being used by terrorists to send dangerous materials such as explosives into the United States.

BACKGROUND OF THE INVENTION

The absence of a comprehensive screening system for cargo, such as air cargo, represents a major soft spot in the current United States security system, such as the air travel security system. A report prepared by the Federal Aviation Administration's office of aviation security research and development in October of 2001 warned of "catastrophic" flaws in the air cargo security system, according to "USA Today" (trademarked) in May of 2002. On Jun. 10, 2002, the "Washington Post" (trademarked) reported that an internal Transportation Security Administration (TSA) analysis described security for cargo on passenger planes as "easily circumvented." The "Washington Post" (trademarked) quoted an internal TSA report as stating: "Cargo is likely to become—and may already be—the primary threat vector in the short term." Still another TSA document placed the risk of a terrorist attack via cargo as high as "35 to 65 percent," according to the "Washington Post". According to an internal assessment, TSA needs to "improve [cargo] security and reduce risk as soon as possible," the Post reported.

Currently as much as forty percent of air cargo is shipped on passenger planes. Only a negligible percentage of cargo is currently screened—as little as two to four percent, according to current Transportation Security Administration head John Magaw. At present the air cargo security system depends almost entirely on "known shipper" rules. While rules have been tightened since October of 2001, there is broad agreement among experts and officials that nothing in the current system guarantees against determined terrorists gaining access to air-bound cargo and planting an explosive device. Given that roughly seventy-five million tons of cargo is shipped by air in the United States annually from scores of airports, the system presents potential attackers with multiple points of vulnerability.

SUMMARY OF THE INVENTION

The present invention in one or more embodiments provides a system that is comprehensive and effective at detecting explosives in cargo or freight, such as air cargo. A cost-effective system is provided which is non-disruptive to shippers of cargo. The system provided in one or more embodiments is capable of virtually guaranteeing the continuous security and integrity of cargo during the storage and transit process. The present invention in one or more embodiments provides a combination of advanced X-ray technology and packaging technology.

The present invention in one or more embodiments comprises the steps of applying X-rays with an X-ray machine to freight and placing a cover on the freight. The step of placing the cover on the freight may include locking the cover on the freight with a lock. The lock may include an electronic memory, which is programmed with a unique code, which identifies the freight and indicates whether the freight has been tampered with.

An alarm may be activated if the X-ray machine detects the presence of unauthorized explosive or hazardous materials within the freight, such as hazardous materials that might be placed in the freight by terrorists. The method, in at least one embodiment may include visually examining the X-ray imagery of the freight when the alarm is activated. The method may include examining the freight by direct visual inspection if the examination of the X-ray imagery of the freight is not satisfactory and notifying law enforcement authorities if the visual examination of the X-ray imagery of the freight reveals a suspected hazardous or explosive material.

The method may further include visually inspecting the cover on the freight and thereby determining if the cover has been tampered with. The method may further include querying the electronic memory on the lock to determine if the freight is satisfactory and to determine if the freight can be loaded onto a carrier vehicle. The carrier vehicle may typically be an aircraft. The carrier vehicle may also be a boat, a truck, a train, or any other vehicle for carrying freight or cargo.

DETAILED DESCRIPTION OF THE DRAWINGS

Figure 1:
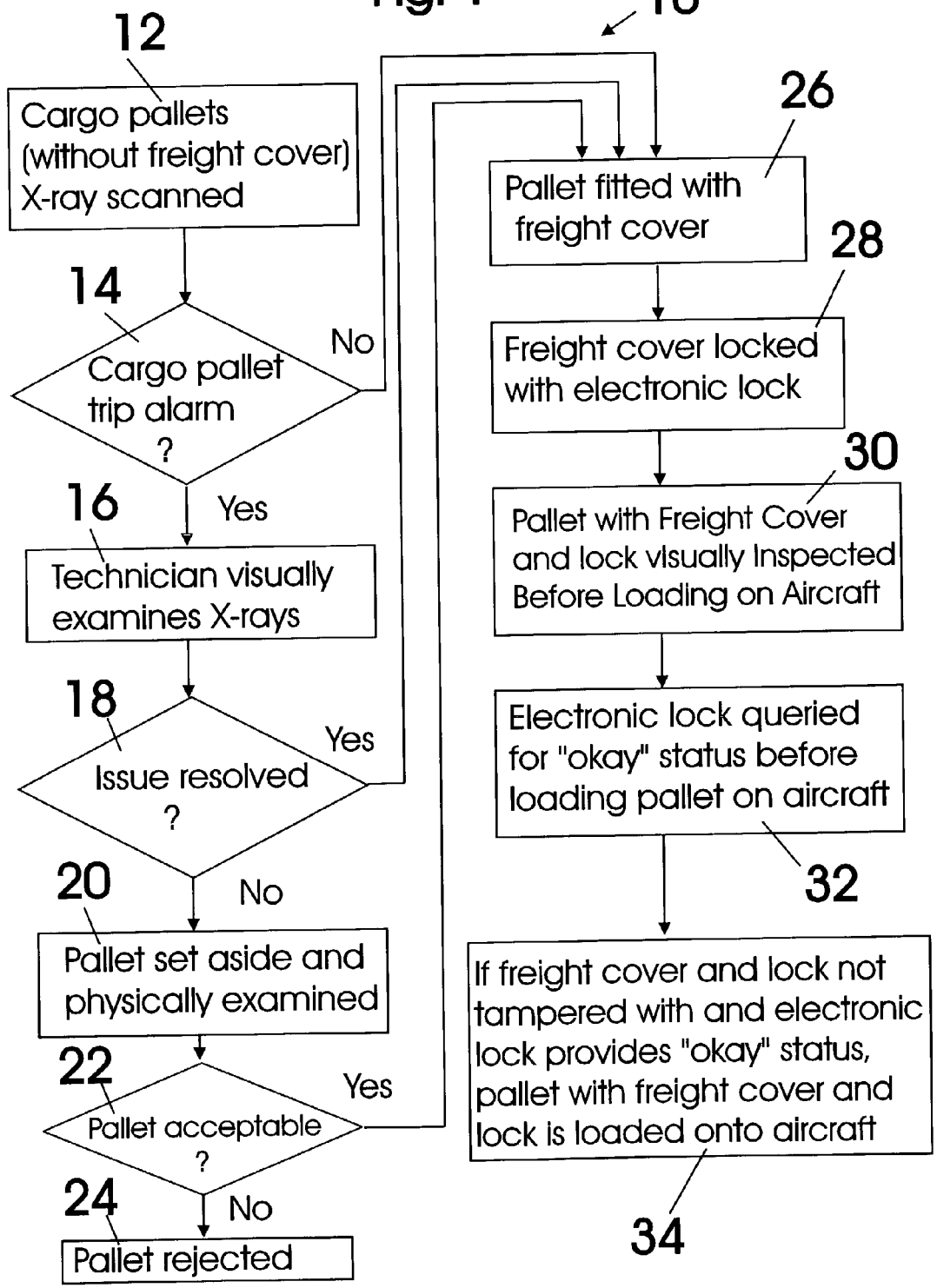
FIG. 1 shows a flow chart of a method in accordance with a first embodiment of the present invention.
Figure 2:
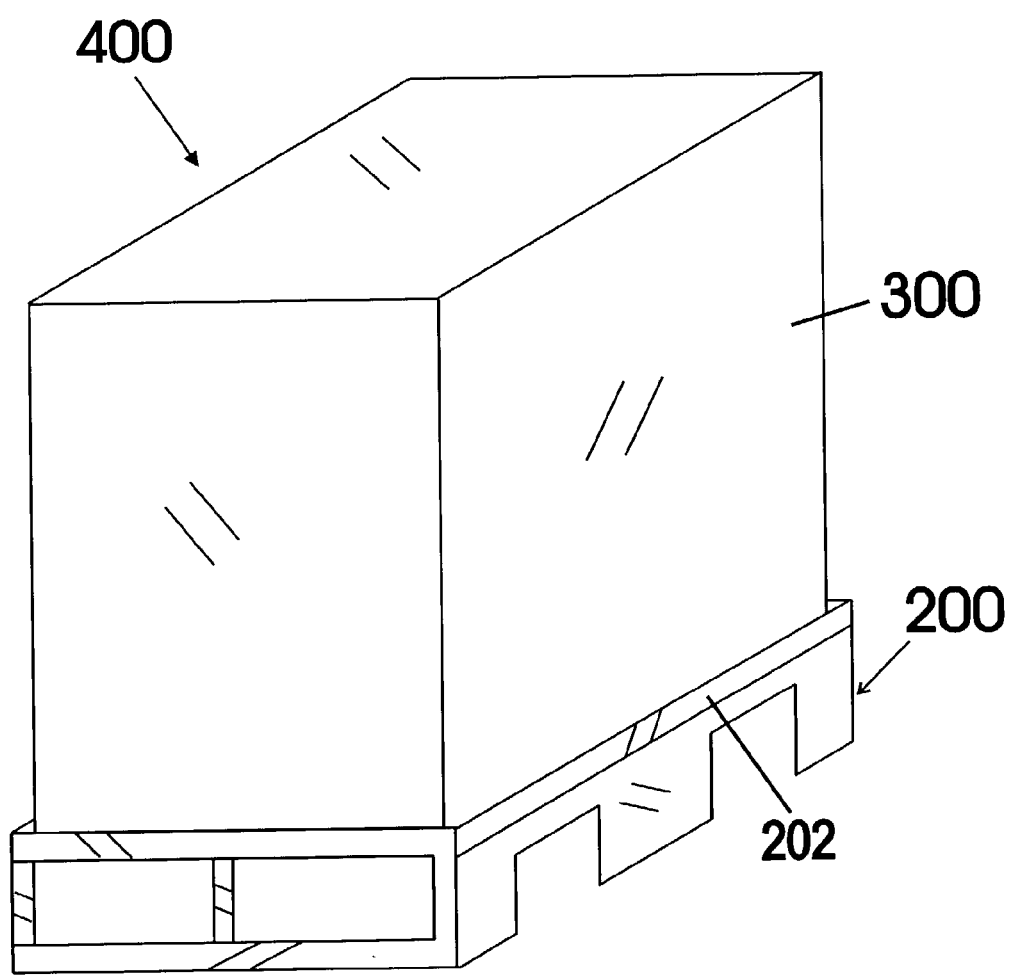
FIG. 2 shows a pallet with freight box or cargo placed on top of the pallet.

FIG. 1 shows a flow chart 10 of a method in accordance with a first embodiment of the present invention. At step 10, a cargo pallet, such as cargo pallet 400 which is comprised of pallet 200 and freight box 300 shown in FIG. 2, is X-ray scanned without a freight cover. The pallet 200 and freight box 300 can be X-ray scanned by a shipper at the shipper's own airport facility or (for smaller shippers) can be X-ray scanned by a multi-shipper location at an airport, train shipping station, bus shipping station, or truck shipping station. X-ray scanning can be performed by an advanced x-ray machine utilizing both backscatter and penetrating x-ray technology. Such technology has proven highly effective in detecting explosives, yielding few "false positives" and virtually no "false negatives." The X-ray machine may be of a type, which scans pallets and their freight at the rate of about twenty per hour, and which provides an automatic audible and/or visual warning if the X-ray machine determines that the cargo pallet 400 contains suspicious materials.

In the event that a cargo pallet 400 trips or activates the alarm of the X-ray machine at step 14, a trained technician next performs an instant visual examination of the X-ray images on the X-ray machine at step 16. If the security issue is not resolved satisfactorily through the initial visual examination of the x-ray imagery at step 18, then the cargo pallet 400 is set aside and carefully physically, manually, and/or directly visually examined at step 20 by a qualified inspector. In general, no more than five out of one hundred cargo pallets (i.e. pallets including cargo) can be expected to trip the alarm of the X-ray machine, and visual inspection of X-ray imagery should be sufficient to resolve the security issue in three of four of such cases. This means that only one to two percent of cargo pallets will be set aside to undergo later lengthier inspection by a qualified security inspector.

If the cargo pallet 400 is not acceptable at step 22 after physical and manual examination at step 20, then cargo pallet 400 is rejected at step 24. The appropriate law enforcement authorities may then be notified to handle a suspicious cargo pallet, such as a cargo pallet suspected of containing explosives.

Figure 3A:
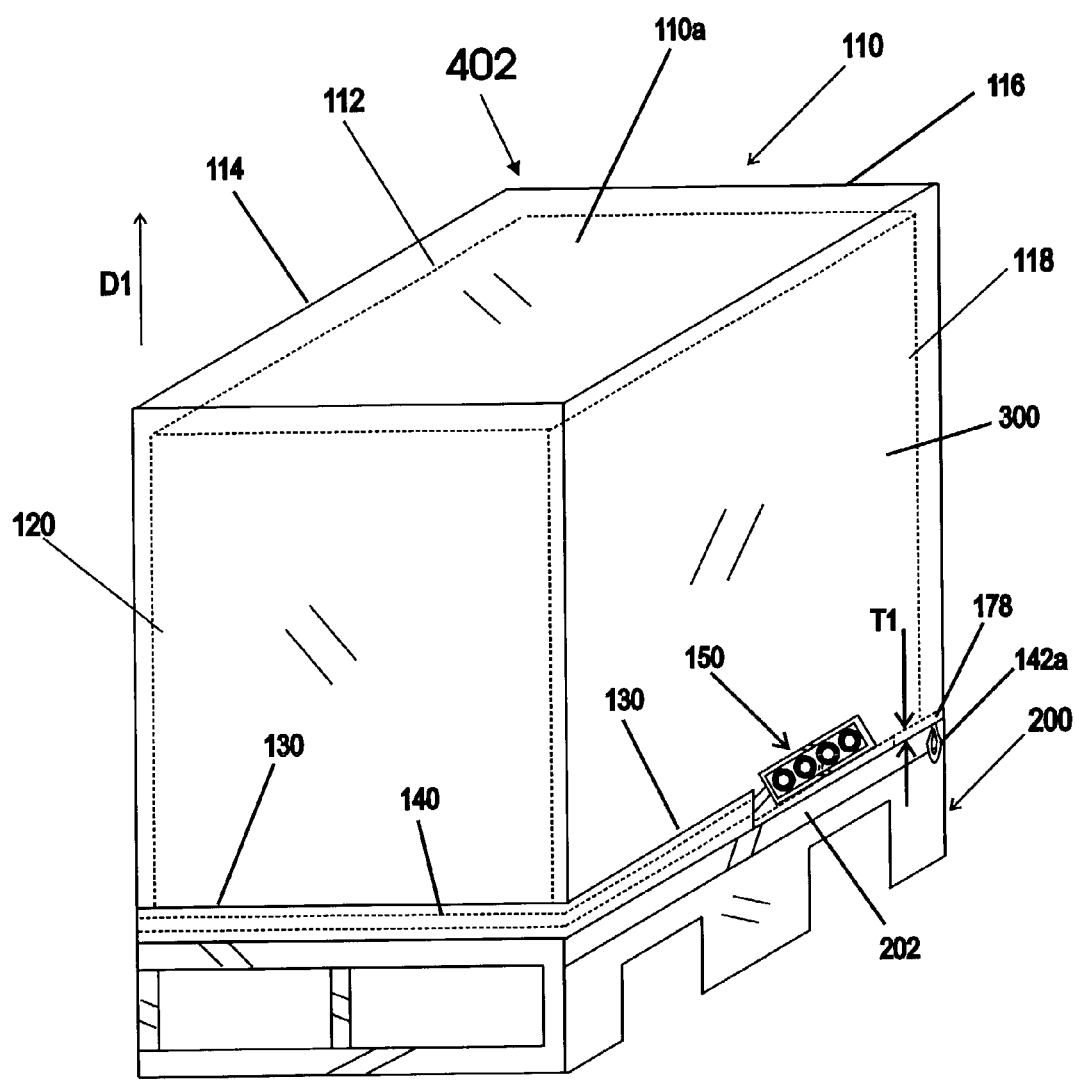
FIG. 3A shows a first perspective view of an apparatus in accordance with an embodiment of the present invention along with a first perspective view of a pallet and the location of a freight box with a first plate of the apparatus inserted between the freight box and the pallet.
Figure 3B:
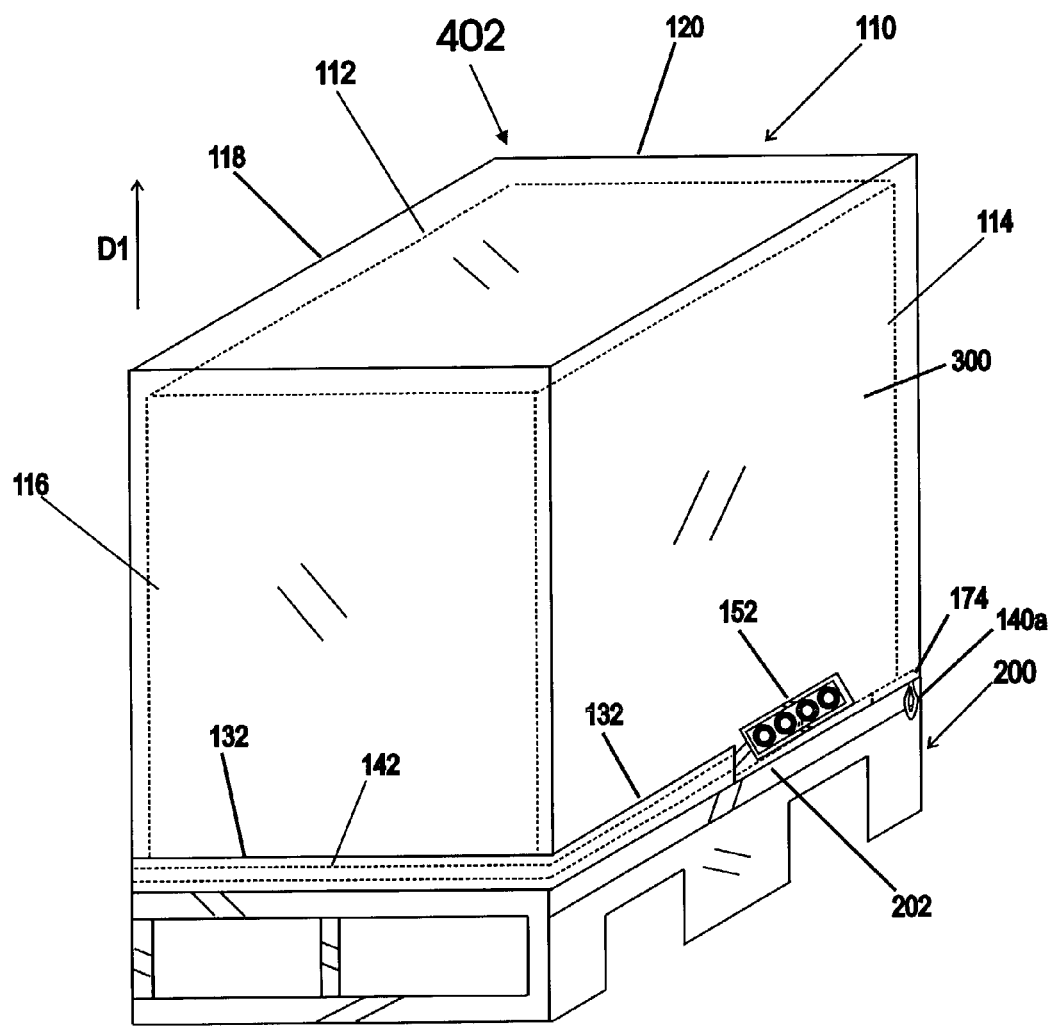
FIG. 3B shows a second perspective view of the apparatus of FIG. 3A and a second perspective view of the pallet of FIG. 3A and the location of a freight box with a second plate of the apparatus inserted between the freight box and the pallet.

If the cargo pallet 400 is determined to be acceptable, i.e. the cargo pallet 400 did not trip the alarm at step 14 or was determined to be acceptable after either visual X-ray examination at step 18, or physical and manual examination at step 22, then the cargo pallet 400 is next immediately fitted with a freight cover at step 26, to form a cargo pallet with freight cover 402, shown in FIGS. 3A and 3B. Typically, the vast majority of cargo pallets (ninety-eight to ninety-nine percent) pass the screening test or tests and are fitted with a freight cover. The freight cover is a durable one, an example of which is apparatus 110, shown by FIGS. 3A–6B and which is the subject of patent application Ser. No. 10/112,233, filed on Mar. 23, 2002 incorporated herein by reference. The freight cover, such as apparatus 110, may cover the freight box 300 on all sides except for the bottom of the freight box 300 which contacts the pallet 200. Alternatively, a freight cover may be provided which covers all sides of the freight box 300 including the bottom of the freight box 300 which contacts the pallet 200. The freight cover, such as apparatus 110 is designed to allow forklifts to continue to move the cargo pallet and freight cover 402 by picking up the pallet 200 and thereby picking up the freight 300 and the freight cover 110. The freight cover 110 is then sealed and/or locked with a tamper-resistant, disposable electronic lock at step 28, such by locks 180 and 184 in the manner shown by FIGS. 3A–6B.

Each electronic lock, such as locks 180 and 184, typically includes a microchip or electronic memory within the lock, which is programmed with a unique encrypted code indicating the contents of the cargo pallet 400 and the "okay" status of the cargo pallet 400. The locked freight cover, such as the apparatus 110 with locks 180 and 184, protects the cargo pallet 400 and particularly the freight 300 from tampering during subsequent storage and transport and provides immediate and obvious visual evidence if tampering has occurred. A terrorist cannot reach the cargo or freight 300 without breaching the freight cover, such as apparatus 110, which will show an obvious tear, or breaking the tamper-resistant electronic lock or locks such as lock 180 and 184. The encrypted electronic code in each lock's chip makes each lock, such as locks 180 and 184, virtually impossible to counterfeit. At the same time, the freight cover 110 should be sufficiently durable not to be breached in normal freight handling. In this case where two locks are used, lock 180 and 184 may have the same unique code.

Cargo, such as freight 300, covered with the freight cover 110, locked with locks 180 and 184, and coded that has satisfactorily passed the X-ray scanning step can then be safely stored at any authorized transportation location, such as an airport location, until actual loading onto the carrier vehicle, such as an aircraft. At the time of loading onto for example aircraft, the freight cover 110 and locks 180 and 184 undergo a visual inspection for tampering at step 30, and the microchip within each lock 180 and 184 should be queried electronically for "okay" status of the cargo pallet 400 at step 32. The locked freight cover 110 plus locks 180 and 184 ensures the integrity of the cargo pallet 400 from the time it is x-rayed and approved until it arrives at its final destination. If the freight cover 110 and locks 180 and 184 are not tampered with and the electronic lock provides an "okay" status, then the cargo pallet 400 with the freight cover 110 and locks 180 and 184 can be loaded onto an aircraft, for example at step 34.

The combination of X-ray and sealed and/or locked freight cover packaging yields a system of maximum efficiency and cost-effectiveness, enabling shippers to achieve a comprehensive X-ray inspection system with minimal disruption to the shipping process and at minimal cost per unit. Because the freight cover 110 and coded lock or locks, such as locks 180 and 184 ensure against tampering during storage and subsequent transit, the scan and freight cover system of embodiments of the present invention gives shippers time flexibility in determining when to schedule X-rays of cargo. This means that X-rays can be scheduled at any time after arrival of the cargo pallet 400 at the airport (or transportation hub or location such as a bus station, train station, or trucking station) and before loading onto the carrier vehicle, such the aircraft. It also allows maximally cost-effective use of X-ray equipment, by enabling smaller shippers to use X-ray equipment of larger shippers and safely move and store the cargo pallet 402 (including freight cover 110 and locks 180 and 184) after X-ray and after freight covering and locking until actual loading on the aircraft or other carrier vehicle.

The use of the sealed, durable, and locked freight cover is an important part to delivering a comprehensive and cost-effective system in at least one embodiment of the present invention. In the absence of the freight cover, cargo would have to be X-rayed at or near the point of loading on the aircraft, or other carrier vehicle, at the time of cargo pallet 400 loading onto the carrier vehicle. Such an approach would require many more X-ray machines, vastly increasing overall costs of the total security system. In addition, the need to X-ray at the time of loading would impose unacceptable delays.

Under the system, method, and apparatus of embodiments of the present invention each X-ray machine can be expected to handle approximately six thousand cargo pallets, such as cargo pallet 400, per month, or roughly two hundred per ten hour day.

For the airport example, a large airport such as JFK airport, shipping approximately 50,000 cargo pallets per month, would require nine to ten X-ray machines. Medium-sized airports, assuming that they ship 20,000 cargo pallets per month, would require about four X-ray machines. Assuming that the one hundred and eleven U.S. cargo certified airports are handling a total of just over three million cargo pallets per month, or 10,000 per hour in a ten-hour day, the entire system could be served by just over five hundred X-ray scan and freight cover systems of embodiments of the present invention. This contrasts very favorably with the thousands of machines that would have to be purchased if cargo pallets were to be x-rayed at or near the point where the cargo pallets are loaded onto the aircraft. In addition, the X-ray scan and freight cover system avoids the delays inherent in point-of-loading screening systems.

Based on these broad assumptions, it is possible to develop an estimate of total system costs, both initial and recurring. Individual x-ray systems may cost $1.2 million installed, with a recurring maintenance cost of about eighteen percent per year. Disposable electronic tamper-resistant locks, of which locks 180 and 184 in FIGS. 6A and 6B may be an example, are typically priced at six dollars each. Durable freight covers, such as apparatus 110 described by FIGS. 3A–6B, for use with the present invention may be twenty dollars each, but at least half can be reused one to three times. Assuming that forty percent of freight covers are used once, twenty percent are used twice, twenty percent are used three times, and twenty percent are used four times, the cost of the glove comes to just over twelve dollars per pallet. Freight cover and lock together add just over eighteen dollars cost per pallet. Cost estimates are listed in Table 1.

TABLE 1

Estimated Costs for
Comprehensive X-ray scan and freight cover cargo security system Initial Costs

| | |
|---|---|
| X-Ray System and Installation | $600 million for 111 airports |

Recurring Costs

| | |
|---|---|
| X-Ray System Maintenance | $108,000 per year for 111 airports |
| Freight Cover | $12 per cargo pallet |
| Tamper-Resistant Electronic Lock | $6 per cargo pallet |

In other words, the initial system can be deployed nationwide for less than $1 billion. On the basis of the above assumptions, the initial cost of deploying x-ray equipment would be $600 million. Ongoing maintenance charges would be $108 million per annum. The freight cover, such as apparatus 110 and lock of the type such as lock 180, assuming only one lock is used, would cost just over $18 per pallet. Finally, there will be the costs of a few personnel to operate the X-ray machine and to inspect suspect cargo pallets. The inspectors would likely be federal employees.

In short, the X-ray scan and freight cover system offers a highly affordable comprehensive solution to a serious immediate security threat.

A further benefit of the present invention in one or more embodiments discloses that a single X-ray scan can cover cargo pallets for the entire transit process. Cargo that transfers aircraft at a second airport will typically undergo the same visual inspection for tampering and electronic querying of the lock, such as shown in FIG. 1 at steps 30 and 32. The cargo typically, does not have to be X-rayed a second time. This also saves costs for shippers.

The present invention in one or more embodiments has the potential of being expanded not only throughout the United States air cargo system, but also abroad, through international agreement. That is, cargo undergoing the same X-ray scan and freight cover inspection regime in the United Kingdom would typically not need to be rescanned and inspected when it arrives for re-transit in the United States.

The invention in one or more embodiments offers protection of cargo against water damage, tampering, and theft and as a result provides insurance savings. A system in accordance with an embodiment of the present invention would provide a comprehensive solution to the problem of securing the U.S. air cargo against terrorism.

Since the X-ray scan and freight cover system integrates existing, well established off-the-shelf technology, the system holds out the prospect of a rapid, relatively inexpensive comprehensive solution to what is widely recognized as an urgent and immediate security threat. The first step to achieving this solution could be a six-month prototype implementation period for integrating, fine-tuning, testing, and certifying the system, such as preferably in a real shipping environment. Once the system has been fine-tuned and tested by the manufacturer and certified by the Transportation Security Agency, it can be deployed nationwide.

The six-month prototype could consist of a single X-ray machine situated in a single airport facility. The prototyping process may include the following steps: (1) System installation and integration: for example an X-ray system may be installed at a selected Emery (trademarked) airport facility. (2) Employee recruitment and training: For example, during this phase, X-ray operators and inspectors may be recruited and trained. Emery (trademarked) employees at the facility may be trained in operation of an X-ray scan and freight cover system in accordance with the present invention. (3) Operational testing: During this phase, all freight and/or pallets at the Emery (trademarked) facility during three separate two-week-long trial periods can be made to undergo the X-ray scan and freight cover process. Time measurements can be taken of the pallet X-ray scanning and freight covering process. Best practices will be developed with an eye to maximizing the efficiency of X-ray scanning and freight covering cargo or freight and minimizing disruption to the shipping process. (4) Component testing: In this phase, performance of individual components can be assessed, including X-ray performance and dependability. Freight cover performance and durability will be carefully assessed. Electronic locks and related equipment can be assessed for performance and durability. Any necessary changes in practices or product design may be introduced. (5) "Red team" testing: In this phase, supervised by the Transportation Security Agency, a "red team" of government agents can first devise and then execute measures designed to defeat or circumvent the system by tampering with cargo and attempt to plant simulated explosive materials. (6) Final testing and certification. The final phase, which can be conducted under TSA supervision, will repeat tests described in steps (2) through (4) as a prerequisite to final certification of the system.

The entire prototyping process can be achieved at a cost of $2 million. At the end of the nine-month period, TSA will have in hand a proven, affordable solution to the threat posed by cargo vulnerability, such as air cargo vulnerability.

Figure 4:
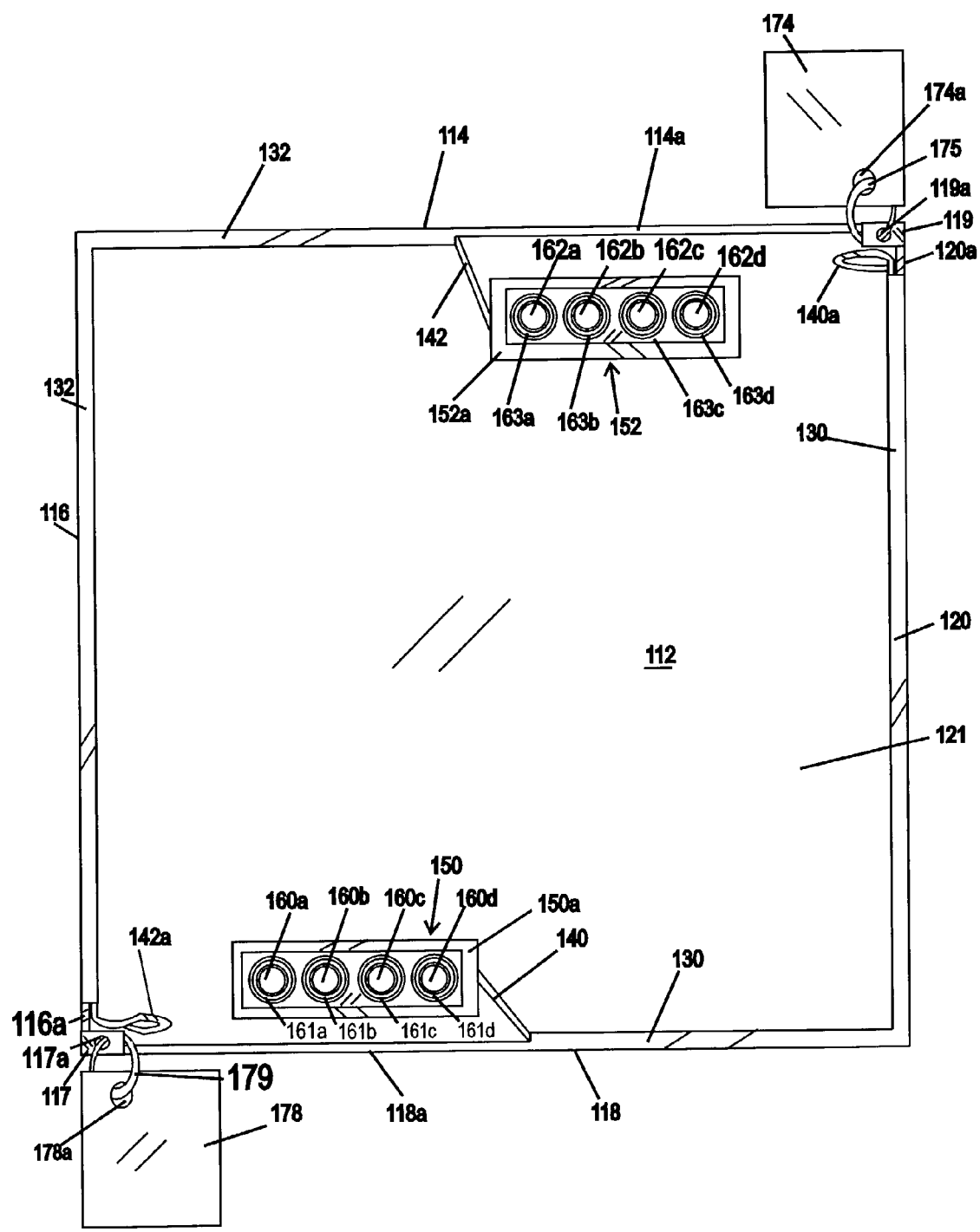
FIG. 4 shows a bottom view of the apparatus of FIG. 3A.

FIG. 3A shows a first perspective view of the apparatus 110 or freight cover, in accordance with an embodiment of the present invention along with a first perspective view of the pallet 200 and the location of the freight box or cargo 300 with a first plate 178 of the apparatus 110 inserted between the freight box 300 and the pallet 200. The apparatus 110 can be considered to be a type of freight cover in accordance with the X-ray scan and freight cover system in various embodiments of the present invention. FIG. 3B shows a second perspective view of the apparatus 110 of FIG. 3A and a second perspective view of the pallet 200 of FIG. 2A and the location of the freight box 300 with a second plate 174 of the apparatus 110 inserted between the freight box 300 and the pallet 200. FIG. 4 shows a bottom view of the apparatus 110 of FIG. 3A.

The apparatus 110 has a top portion 112, and sides 114, 116, 118, and 120. The top portion 112 and sides 114, 116, 118, and 120 may be said to define an enclosure having an opening. The enclosure may be said to enclose a chamber 110a defined by top portion 112, and sides 114, 116, 118, and 120. Inside the chamber 110a is located a freight box 300. The freight box 300 may be, for example, a box for a refrigerator or a box for an oven or any other box holding any other type of goods or freight. The freight box 300 may be replaced by any other type of freight or cargo such as a plurality of smaller freight boxes.

The apparatus 110 also includes straps 140 and 142. Each of the straps 140 and 142 may be a rope, a cord, a strap, or a similar device. The strap 140 is fixed, at its first end, to an attachment device 150, as shown in FIG. 3A. The strap 142 is fixed at its first end, to an attachment device 152, as shown in FIG. 3B. Most of the strap 140 is shown in dashed lines and lies inside of a sleeve 130 which is fixed at the bottom of sides 120 and 118 as shown in FIG. 3A. Most of the strap 142 lies inside of a sleeve 132 which is fixed at the bottom of sides 116 and 114 as shown in FIG. 3B. The strap 140 ends in a loop 140a at the second end of the strap 140, as shown in FIG. 3B. Similarly the strap 142 ends in a loop 142a at the second end of the strap 142, as shown in FIG. 3A.

As shown in FIG. 4, the attachment device 152 includes openings 162a, 162b, 162c, and 162d formed in rings 163a, 163b, 163c, and 163d. Similarly, the attachment device 150 includes openings 160a, 160b, 160c, and 160d formed in rings 161a, 161b, 161c, and 161d. Each of the rings 161a–d and 163a–d may be metal rings. Each of the rings 161a–d and each of the rings 163a–d are fixed to a base material 150a and 152a, respectively, of the attachment devices 150 and 152, respectively. Each of the rings 161a–d and 163a–d may be comprised of three sections, which may be an outer section, a middle section, and an inner section. The sides 114, 116, 118, and 120, the top portion 112, and the base material 150a and 152a may be made of the same material which may be TYVEK (trademarked) or any other water resistant and/or durable material.

In FIG. 4, a ring 175 is shown inserted through a hole 174a in the plate 174, and the ring 175 is thereby connected to the plate 174. Similarly a ring 179 is shown inserted through a hole 178a in the plate 178, and the ring 179 is thereby connected to the plate 178. The ring 175 is also shown inserted into a hole 119a in a sleeve 119. The sleeve 119 is fixed to the sides 114 and 120 of the apparatus 110. Similarly, the ring 179 is also shown inserted into a hole 117a in a sleeve 117. The sleeve 117 is fixed to the sides 116 and 118 of the apparatus 110.

In operation, an individual would place the apparatus 110 over freight or cargo, such as the freight box 300, which is sitting on the pallet 200, so that the freight is completely covered by the apparatus 110. In this manner the apparatus 110 is positioned as in FIGS. 3A and 3B. The apparatus 110 has an open end 121 whose location is shown in FIG. 4, which is like the open end of an open box. The plates 174 and 178 are then slid under the freight box 300, substantially at the corners of the apparatus 110 as shown in FIGS. 3A and 3B. Each of the plates 174 and 178 may have a thickness, T1 shown in FIG. 3A, of ⅛ (one eighth) of an inch.

Figure 5A:
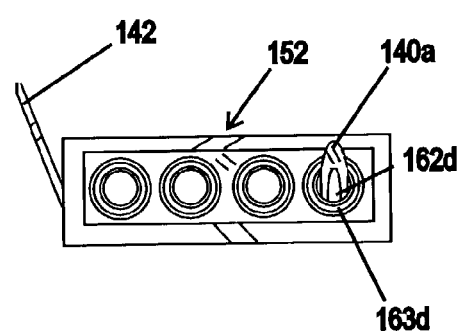
FIG. 5A shows a first attachment device of the apparatus of FIG. 3A with a first loop inserted into a first ring of the first attachment device.
Figure 5B:
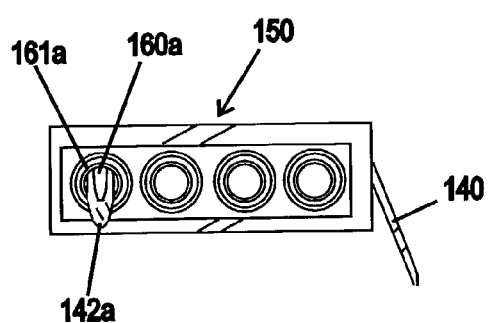
FIG. 5B shows a second attachment device of the apparatus of FIG. 3A with a second loop inserted into a first ring of the second attachment device.
Figure 6A:
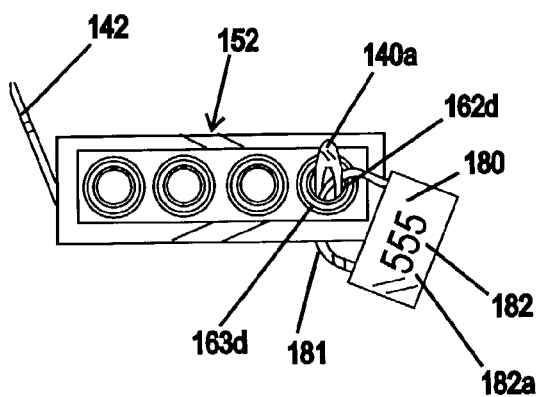
FIG. 6A shows a first lock which has been inserted into the first loop and the first ring of the first attachment device so that the first loop is attached to the first attachment device.
Figure 6B:
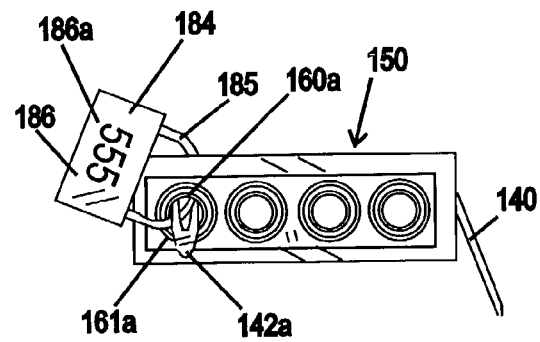
FIG. 6B shows a second lock which has been inserted into the second loop and the first ring of the second attachment device so that the second loop is attached to the second attachment device.

The individual would then insert loop 140a into one of the openings 162a–d of the attachment device 152, such as into opening 162d as shown in FIG. 5A. Similarly, the individual would insert loop 142a into one of the openings 160a–d of the attachment device 150, such as into opening 160a as shown in FIG. 5B. The individual would then insert a loop 181 of a lock 180 through the loop 140a and the opening 162d so that the strap 140 is connected to the attachment device 152 at the end where loop 140a is located, as shown in FIG. 6A. The loop 181 would be pressed into the base 182 to lock the lock 180. Similarly the individual would insert a loop 185 of a lock 184 through the loop 142a and the opening 160a so that the strap 142 is connected to the attachment device 150 at the end where loop 142a is located, as shown in FIG. 6B. This causes the straps 140 and 142 to be connected together and tightened so that the sides 114, 116, 118 and 120 fit snugly around the perimeter of the freight box 300.

Locks 180 and 184 have serial numbers 182a and 186a, respectively, which are both "555". This can be used as an identification number for the particular freight box 300 or the pallet 200. The pallet 200 may be any type of pallet having and may have a base 202.

The apparatus 110 protects freight, such as freight box 300 lying within the chamber 110a enclosed by top 112, and sides 114, 116, 128, and 120 from water damage, from theft, and from the high insurance costs associated with water damage and theft. The apparatus 110 is made of durable, lightweight, resistant material such as TYVEK (trademarked). The apparatus 110 is typically one piece. The apparatus 110 protects freight far better than typical plastic wrappings. Plastic wrappings may allow water to penetrate the freight. Further plastic wrappings are easy for a thief to open and to steal from and to reapply plastic wrapping without detection.

The locks 180 and 184 typically have to be broken for a thief to obtain access to the freight box 300 inside the apparatus 110. If the locks 180 or 184 are broken it provides evidence of tampering of the freight box 300 and/or the apparatus 110. In one embodiment of the present invention, the locks 180 and 184 are of the form such that once they are opened, they cannot be resealed. In accordance with an embodiment of the present invention, each palette or each collection of freight on a palette, may have its own apparatus 110 and at least one lock, like lock 180 or 184, with a unique serial number.

Because tampering can easily be detected, an insurance company can easily determine when the apparatus 110 was tampered with and if necessary, appropriately ascertain liability for the damage to the freight. The apparatus 110 acts, as an effective deterrent against would be thieves.

Figure 7:
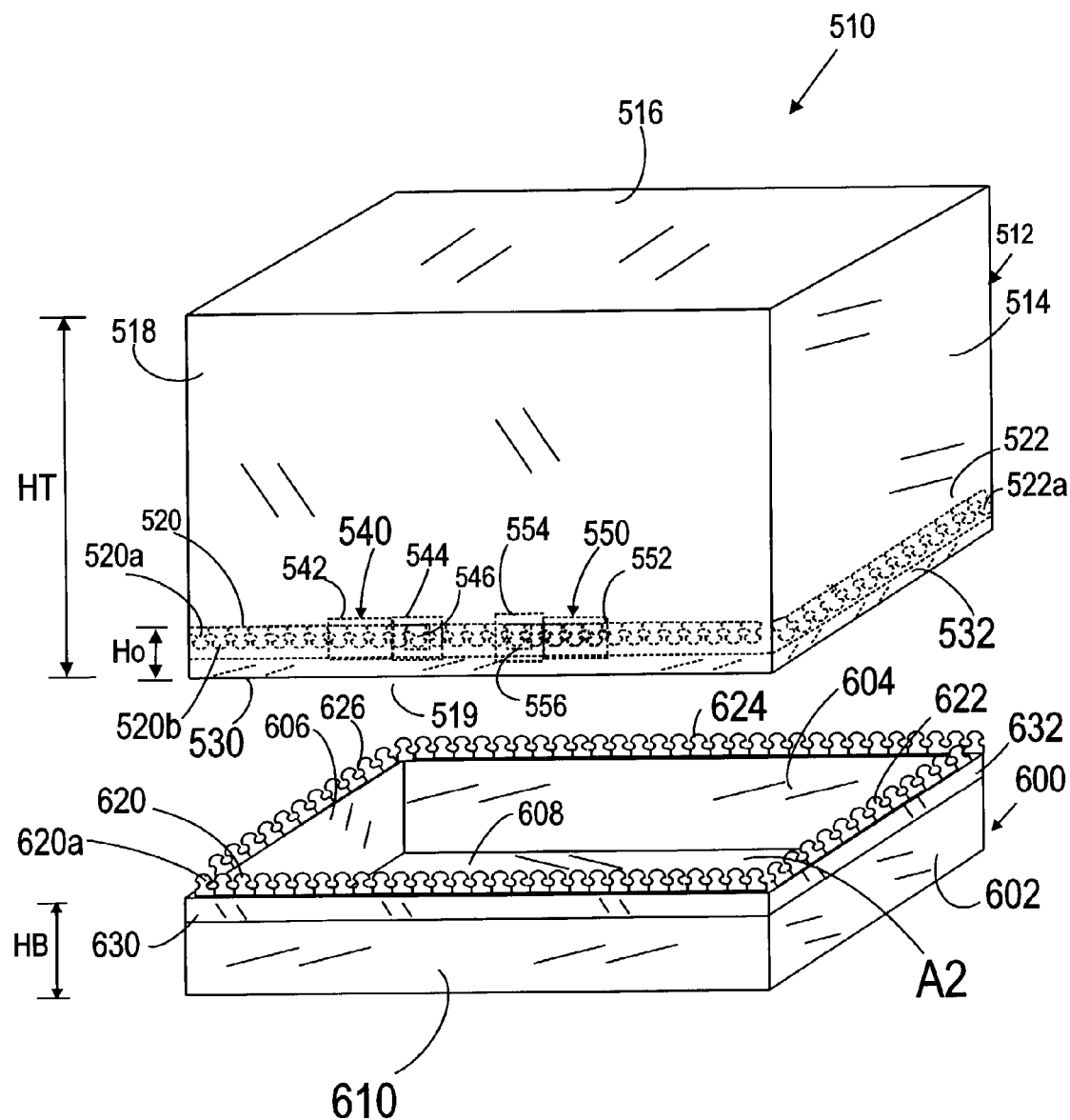
FIG. 7 shows a perspective view of a freight enclosure or freight cover for use in accordance with another embodiment of the present invention including a top portion and a bottom portion with the top portion and bottom portion separated.
Figure 8:
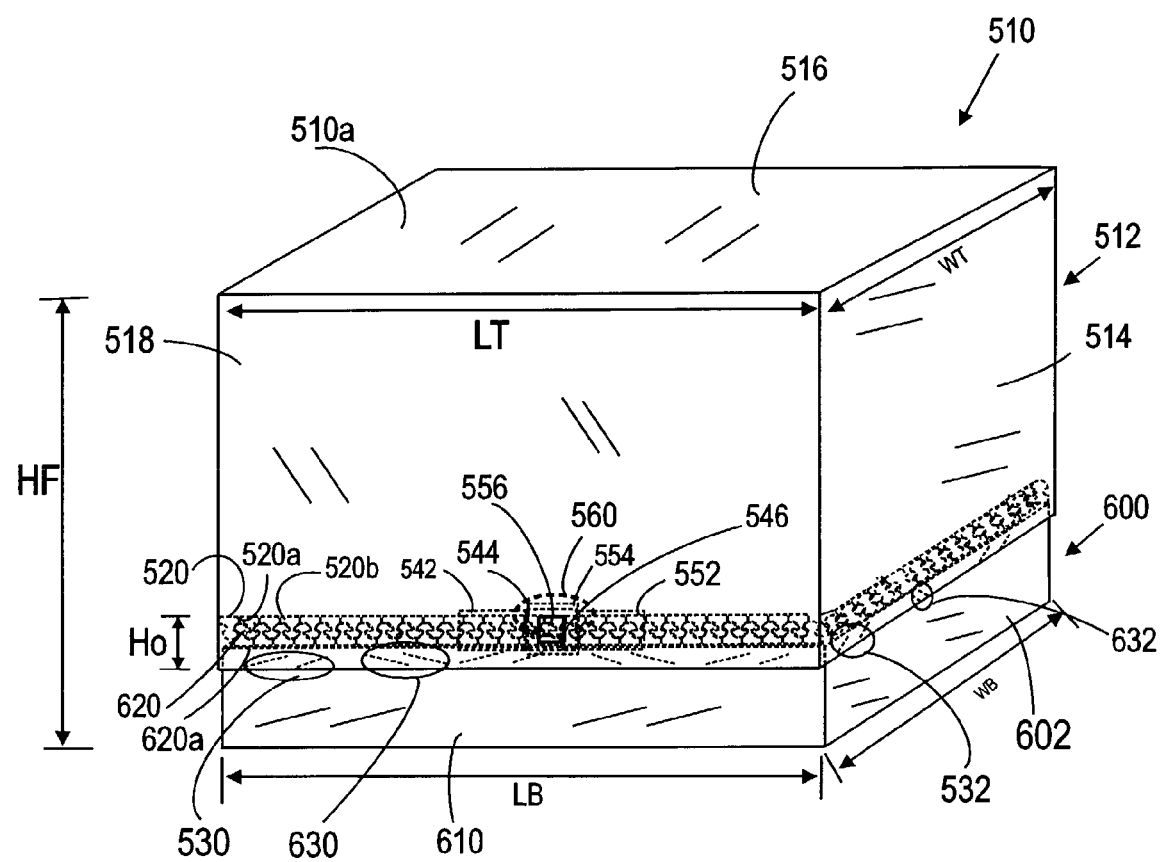
FIG. 8 shows a perspective view the freight enclosure or freight cover of FIG. 7 with the top and bottom portions attached together.

FIG. 7 shows a perspective view of a freight enclosure or freight cover 10 for use in accordance with another embodiment of the present invention including a top portion 512 and a bottom portion 600 with the top portion 512 and the bottom portion 600 shown separated. FIG. 8 shows a perspective view the freight enclosure 510 of FIG. 7 with the top portion 512 and the bottom portion 600 attached together. The top portion 512, as shown in FIG. 7, has a box structure. The top portion 512 is comprised of side 514 (and an opposite side not shown), side 518 (and an opposite side not shown), and top side 516. The side 514 (and its opposing side), side 518 (and its opposing side), and top side 516 form enclose a first area. The top portion 512 can be placed on top of freight, an object, or a package, so that the freight, object or package, lies inside the first area enclosed by the sides 514 and 518 (and their opposing sides) and the top side 516.

Side 518 of the top portion 512 is comprised of a VELCRO (trademarked) section 530 which may be comprised of hooks or loops of a VELCRO (trademarked) system. The VELCRO (trademarked) section 530 may be thought of as a section of a sealing device in accordance with the present invention. Similarly, side 514 of the top portion 512 is comprised of a VELCRO (trademarked) section 532 which may be comprised of hooks or loops of a VELCRO (trademarked) system. The VELCRO (trademarked) section 532 may be thought of as a section of a sealing device in accordance with the present invention. The VELCRO (trademarked) sections 530 and 532, in the embodiment shown in FIG. 7, lie inside the first area enclosed by the sides 514 and 518 (and their opposing sides) and top side 516. There can also be a VELCRO (trademarked) section on the side opposite to side 518 near the bottom of that side, similar to opposing VELCRO (trademarked) section 530, which also lies inside the box structure of top portion 512. There can also be a VELCRO (trademarked) section on the side opposite side 514 near the bottom of that side, similar to opposing VELCRO (trademarked) section 532, which also lies inside the box structure of top portion 512. The VELCRO (trademarked) sections 530 and 532 on the top portion 512 are shown in dashed lines to show that they are inside the box structure of top portion 512.

The top portion 512 is also comprised of a first set of zipper teeth comprised of portions 520 and 522. Portion 520 of the first set of zipper teeth has a plurality of zipper teeth (such as tooth 520a), which are attached to the side 518 of the top portion 512. The side opposing side 518 (not shown) also has a plurality of corresponding zipper teeth, not shown. Portion 522 of the first set of zipper teeth has a plurality of zipper teeth (such as tooth 522a), which are attached to the side 514 of the top portion 512. The side opposing side 514 (not shown) also has a plurality of corresponding zipper teeth, not shown. The zipper teeth of portions 520 and 522 and their opposing portions not shown, are seamlessly connected so that a zipper or zippers can move around the entire freight enclosure 510 along the first set of zipper teeth.

The top portion 512 may be made of a durable waterproof fabric material, such as TYVEK (trademarked), which was created by DUPONT. TYVEK is a lightweight durable fabric that can withstand the punishment of the elements of the weather and of heavy usage. The first set of zipper teeth, including teeth on the sides 514 and 518 and their opposing sides, can be sewn into the fabric material of top portion 512. The first set of zipper teeth can be sewn inside the first area enclosed by the sides 514 and 518 (and their opposing sides) and tip side 516. I.e. the first set of zipper teeth, in one embodiment, would not normally be able to be seen from the perspective shown by FIG. 7 (unless the TYVEK material of top portion 512 is transparent), and for that reason in FIG. 7, the plurality of teeth 520 and 522 are shown in dashed lines.

FIG. 7 also shows a first zipper 540 and a second zipper 550. The zippers 540 and 550 are connected to the teeth 520 and also lie inside the enclosed first area bounded by the sides 514 and 518 (and their opposing sides) and top side 516. For that reason the zippers 540 and 550 are shown in dashed lines also, because normally the zippers 540 and 550 could not be seen from the perspective shown by FIG. 7.

Zippers 540 and 550 include attachment portions 542 and 552 which attach the respective zippers to the first set of zipper teeth, for example at portion 520. Zippers 540 and 550 may include loop portion 544 having an opening 546 and loop portion 554 having an opening 556, respectively.

The bottom portion 600 also has a box structure. The bottom portion 600 is comprised of sides 602, 604, 606, and 610, and bottom side 608. The sides 602, 604, 606, 610, and 608 bound an enclosed area A2 shown in FIG. 7. Side 610 of the bottom portion 600 is comprised of a VELCRO (trademarked) section 630 which may be comprised of hooks or loops of a VELCRO (trademarked) system. The VELCRO (trademarked) section 630 may be thought of as a section of a sealing device in accordance with the present invention. Similarly, side 602 of the bottom portion 600 is comprised of a VELCRO (trademarked) section 632 which may be comprised of hooks or loops of a VELCRO (trademarked) system. The VELCRO (trademarked) section 632 may be thought of as a section of a sealing device in accordance with the present invention. The VELCRO (trademarked) sections 630 and 632, in the embodiment shown in FIG. 7, lie outside the area A2. There can also be a VELCRO (trademarked) section on the side 604 near the top of the side 604, similar to opposing VELCRO (trademarked) section 620, which also lies outside the area A2. There can also be a VELCRO (trademarked) section on the side 606 near the top of the side 606, similar to opposing VELCRO (trademarked) section 632, which also lies outside the area A2.

The bottom portion 600 also includes a second set of teeth comprised of portions 620, 622, 624, and 626. The second set of teeth (portions 620, 622, 624, and 626) on bottom portion 600 is designed to mesh with the first set of teeth on the top portion 512 comprised of portion 520 and its opposing portion not shown, and portion 522 and its opposing portion not shown as shown by FIG. 8. The zippers 540 and 550 are used to connect the first set of teeth of top portion 512 with the second set of teeth of bottom portion 600 to thereby cause top portion 512 to be connected to bottom portion 600 as shown in FIG. 8.

The top portion 512 of the freight enclosure 510 has a height of HT, which may be 59 inches. The bottom portion 600 has a height HB that may be 14 inches. When the top portion 512 and the bottom portion 600 are zipped together, as shown in FIG. 8, the top portion 512 overlaps the bottom portion 600 by a distance H0, which may be about three inches. The distance H0 corresponds to the approximate internal location of the first set of teeth on the top portion 512 which are located about three inches up from an edge, such as edge 519 for side 518 shown in FIG. 7. After the top portion 512 and bottom portion 600 have been zipped together the freight enclosure 510 has a final height of HF, which may be seventy inches. The side 518 of top portion 512 may have a length LT that may be one hundred and thirty inches. The side 610 of the bottom portion 600 may have a length LB, shown in FIG. 8, which may be slightly less than the length LT of the top portion 512 to allow the top portion 512 to overlap the bottom portion 600. For example, LB may be one hundred and twenty-nine inches. A close fit should be provided.

The side 514 of the top portion 512 may have a width WT that may be 93 inches. The side 602 of the bottom portion 600 may have a width WB that may be slightly less than 93 inches, such as for example 92 inches, again to allow top portion 512 to overlap bottom portion 600.

In operation, an individual would place the freight or package onto bottom side 608 of the bottom portion 600. The freight enclosure 510 is particularly useful for enclosing freight loaded on a large pallet. The freight should be placed and should be of a size so that the top portion 512 can be placed on top of the freight and joined with the bottom portion 600 as shown in FIG. 8. The freight will lie in the combination enclosed area of the freight enclosure 510 which is bounded by top side 516, sides 514 and 518 (and their opposing sides) of top portion 512 and bottom side 608, sides 602, 604, 606, and 610 of the bottom portion 600.

The top portion 512 is placed over the freight and then zipped together to the bottom portion 600 by sliding the zippers 540 and 550 over the teeth 620, 622, 624, and 626 on the bottom portion 600 until all or virtually all of the first set of teeth on top portion 512 are linked to their appropriate partners on the second set of teeth on the bottom portion 600. For example, in FIG. 2, tooth 620a of the second set of teeth on bottom portion 600 is linked to teeth 520a and 520b of the first set of teeth on top portion 512. The first and second sets of teeth can be considered to be part of a connection device for connecting the top portion 512 and the bottom portion 600.

After all the first set of teeth and the second set of teeth are linked together, the zippers 540 and 550 are brought closely together so that the loops 544 and 554 overlap and opening 546 is on top of opening 556. At that point a ring or lock 560 may be placed through the openings 546 and 556 and used to join the zippers 540 and 550 so that the zippers 540 and 550 are connected together. The lock 560 may then be locked. The lock 560 may have a code or serial number attached or engraved on it which may be unique for this piece of freight, or pallet, or this particular freight enclosure 510.

Once the lock 560 has been sealed, a flap is used to cover the joined first set of zipper teeth (520, 522, and those teeth opposite 520 and 522 on top portion 512) and the second set of zipper teeth (620, 622, 624, and 626). The "flap" is a part of the top portion 512 which may include the section on side 518 having a height H0 from end 519 to the location where the teeth 520 are sewn (and may also include similarly located sections on side 514, and on opposing sides opposite of side 514 and 518). The "flap" part of top portion 512 may include a VELCRO (trademarked) portion, which may include VELCRO (trademarked) portions 530 and 532 on sides 518 and 514 as well as VELCRO (trademarked) portions on opposing sides not shown. The VELCRO (trademarked) portions such as 530 and 532 may be located inside the box structure of the top portion 512 (i.e. bound by the sides 514 and 518 and their opposing sides and side 516). The purpose of this flap and additional VELCRO seal is to insure that no water may penetrate the joined first set of zipper teeth (520, 522, and opposing teeth) and the second set of zipper teeth (620, 622, 624, and 626). THE VELCRO sections 530 and 532 (and opposing portions join with VELCRO sections 630, 632, and opposing portions respectively on the bottom portion 600 as shown by FIGS. 7 and 8.

Following locking of the lock 560, and the sealing of the VELCRO flap the freight enclosure 510 is ready for transport.

The lock 560 can be a metal seal of a type that once it has been opened it can not be relocked. In this manner, a person receiving the freight enclosure can tell whether the lock 560 and therefore the freight enclosure 510 contents have been tampered with or the contents removed.

The immediately previous sending agent, therefore, can be absolved of liability for any missing or damaged freight discovered at a later time. As each receiving agent is asked to sign for the freight, he need only to check that the lock 560 is intact, that the freight enclosure 510 has does not have any rips, and that the serial number is correct. If so, that he can sign with assurances. If the lock is broken, the pallet has possibly been tampered with, and a signature is not made until an inspection is concluded, with any missing or damaged freight attributable to the previous agent. Additionally, if there are any rips in the material, the agent may assume potential damage or theft has occurred. As this is not plastic wrapping, which is easily ripped or sliced open, tears may not be concealed by mere tape, as is common with plastic wrapping. If a pilferer attempts to slice open the Glove and cover it up with tape, the next agent will see the tape as a warning that there has been tampering. This serves as an extremely effective deterrent to would-be thieves.

In accordance with a method of an embodiment of the present invention, at each stage of transport of a freight enclosure 510, an agent can check to see if the metal seal 560 or lock 560 has been tampered with. If it has not been tampered with, the agent can note this fact in a log sheet. Thus, it is possible to know during exactly what stage of transport tampering occurred. An agent receiving the enclosure 510 need only to check that the lock 560 is in tact and that the serial number is correct.

The waterproof aspect of an embodiment of the present invention eliminates water damage to the freight inside the enclosure 510 when the freight enclosure 510 is exposed to rain, snow or other liquid accumulation. This assumes there are no lacerations to the freight enclosure 510. The enclosure 510 may be comprised of Tyvek (for all the sides of both the top portion 512 and the bottom portion 600), which is a strong fabric used in the manufacturing of backpacks, tents and tarps. The United States military currently uses Tyvek for these and other purposes.

Although the invention has been described by reference to particular illustrative embodiments thereof, many changes and modifications of the invention may become apparent to those skilled in the art without departing from the spirit and scope of the invention. It is therefore intended to include within this patent all such changes and modifications as may reasonably and properly be included within the scope of the present invention's contribution to the art.

I claim:

1. A method of screening and protecting freight prior to transportation on a carrier, the method comprising the steps of:
   a. applying x-rays with an x-ray machine to freight to detect the presence of hazardous substances in the freight, the x-ray machine having an alarm which is activated if hazardous substances are detected;
   b. covering the freight with a flexible, durable, water-impervious cover if the freight does not activate the alarm, the cover comprising a top portion and first, second, third and fourth sidewalls joined at their upper ends to the top portion and joined at their respective sides to an adjacent sidewall so that the top portion and sidewalls together form an open box-shaped structure which fits over and covers the freight each of the sidewalls also having a bottom edge, the cover further comprising fastening means for securing the cover to the freight, wherein the fastening means comprises a first strap positioned along the bottom edge of at least the first sidewall, and a second strap positioned along the bottom edge of at least the third sidewall, the first strap having first end connected to an attachment device and a second end terminating in a loop, the second strap having a first end connected to an attachment device and a second end terminating in a loop, wherein the attachment devices of the first and second straps each comprise a handle having a plurality of spaced apart ringed openings therethrough, and wherein the cover is secured to the freight by inserting the loop of the first strap through one of the ringed openings in the handle of the second strap, and by inserting the loop of the second strap through one of the ringed openings in the handle of the first strap; and c. applying a locking device to the fastening means and locking the locking device to lock the cover on the freight.

2. The method of claim 1 wherein the locking device includes an electronic memory which is programmed with a unique code which identifies the freight and indicates whether it has been tampered with.

3. The method of claim 2 further comprising the step of querying the electronic memory to determine if the freight is satisfactory and to determine if the freight can be loaded onto the carrier.

4. The method of claim 3 further comprising the step of visually inspecting the cover secured to the freight to determine whether the cover is intact and the freight can be loaded onto the carrier.

5. The method of claim 1 further including the steps of visually inspecting and analyzing x-ray imagery of the freight if the alarm is activated to determine whether hazardous substances are present in the freight, covering the freight with the flexible, durable water-impervious cover if no hazardous substances are detected from the visual inspection of the x-ray imagery, and applying the locking device to the fastening means to lock the cover on the freight.

6. The method of claim 1 further including the step of visually inspecting the freight if the alarm is activated to determine whether hazardous substances are present in the freight, covering the freight with the flexible, durable, water-impervious cover if no hazardous substances are determined from the visual inspection of the freight, and applying the locking device to the fastening means to lock the cover on the freight.

7. The method of claim 1 wherein a locking device is inserted through the loop of the first strap and the ringed opening in the handle of the second strap and locked, and a locking device is inserted through the loop of the second strap and the ringed opening in the handle of the first strap and locked to lock the cover on the freight.

8. A system for screening and protecting freight prior to transportation on a carrier, the system comprising:

an x-ray machine for applying x-rays to freight, the x-ray machine being capable of detecting hazardous substances in the freight and having an alarm which is activated if hazardous substances are detected;

a flexible, durable, water-impervious freight cover for covering the x-rayed freight, the cover comprising a top portion and first, second, third and fourth sidewalls joined at their upper ends to the top portion and joined at their respective sides to an adjacent sidewall so tat the top portion and sidewalls together form an open box-shaped structure which fits over and covers the freight, each of the sidewalls also having a bottom edge, the cover further comprising fastening means for securing the cover to the freight, wherein the fastening means comprises a first strap positioned along the bottom edge of at least the first sidewall, and a second strap positioned along the bottom edge of at least the third sidewall, the first strap having a first end connected to an attachment device and a second end terminating in a loop, the second strap having first end connected to an attachment device and a second end terminating in a loop, wherein the attachment devices of the first and second straps each comprise a bundle having a plurality of spaced apart ringed openings therethrough, and wherein the cover is secured to the freight by inserting the loop of the first strap through one of the ringed openings in the handle of the second strap, and by inserting the loop of the second strap through one of the ringed openings in the handle of the first strap; and a locking device applied to the fastening means for locking the cover to the freight.

9. The system of claim 8, wherein the locking device includes an electronic memory which is programmed with a unique code which identifies the freight and indicates whether it bus been tampered with.

10. The system of claim 8 wherein a locking device is inserted through the loop of the first strap and the ringed opening in the handle of the second strap and locked, and a locking device is inserted through the loop of the second strap and the ringed opening in the handle of the first strap and locked to lock the cover on the freight.

* * * * *